US010577385B2

(12) United States Patent
Han et al.

(10) Patent No.: US 10,577,385 B2
(45) Date of Patent: Mar. 3, 2020

(54) GROUP 5 METAL COMPOUND, METHOD FOR PREPARING THE SAME, PRECURSOR COMPOSITION FOR DEPOSITING LAYER CONTAINING THE SAME, AND METHOD FOR DEPOSITING LAYER USING THE SAME

(71) Applicant: UP CHEMICAL CO., LTD., Pyeongtaek-si, Gyeonggi-do (KR)

(72) Inventors: Won Seok Han, Pyeongtaek-si (KR); Myeong-Ho Park, Suwon-si (KR); Dae-Young Kim, Pyeongtaek-si (KR); Jun Hwan Choi, Goyang-si (KR)

(73) Assignee: UP CHEMICAL CO., LTD., Pyeongtaek-si, Gyeonggi-Do (KR)

( * ) Notice: Subject to any disclaimer, the term of this patent is extended or adjusted under 35 U.S.C. 154(b) by 0 days.

(21) Appl. No.: 16/296,395

(22) Filed: Mar. 8, 2019

(65) Prior Publication Data
US 2019/0202847 A1 Jul. 4, 2019

Related U.S. Application Data

(63) Continuation of application No. PCT/KR2017/009188, filed on Aug. 23, 2017.

(30) Foreign Application Priority Data

Sep. 8, 2016 (KR) ........................ 10-2016-0115708

(51) Int. Cl.
| | |
|---|---|
| *C07F 9/00* | (2006.01) |
| *C23C 16/18* | (2006.01) |
| *H01L 21/285* | (2006.01) |
| *C23C 16/34* | (2006.01) |
| *C07F 17/00* | (2006.01) |
| *C23C 16/455* | (2006.01) |
| *C23C 16/40* | (2006.01) |
| *H01L 21/02* | (2006.01) |
| *H01L 21/28* | (2006.01) |

(52) U.S. Cl.
CPC ............ *C07F 9/00* (2013.01); *C07F 17/00* (2013.01); *C23C 16/18* (2013.01); *C23C 16/34* (2013.01); *C23C 16/40* (2013.01); *C23C 16/405* (2013.01); *C23C 16/455* (2013.01); *C23C 16/45553* (2013.01); *H01L 21/02* (2013.01); *H01L 21/28* (2013.01); *H01L 21/285* (2013.01)

(58) Field of Classification Search
CPC . C07F 9/00; C07F 17/00; C23C 16/18; C23C 16/45525; H01L 21/285
See application file for complete search history.

(56) References Cited

U.S. PATENT DOCUMENTS

| | | | | |
|---|---|---|---|---|
| 5,981,667 A * | 11/1999 | Asakura | ................ | C08F 279/02 525/243 |
| 6,414,088 B1 * | 7/2002 | Tanaka | ........................ | C08J 5/18 525/191 |
| 9,691,771 B2 * | 6/2017 | Lansalot-Matras | ......................... | H01L 27/1085 |
| 2002/0099155 A1 * | 7/2002 | Inoue | ....................... | C08F 10/00 526/172 |
| 2009/0143548 A1 * | 6/2009 | Shiba | ....................... | C08C 19/10 526/92 |
| 2013/0150642 A1 * | 6/2013 | Sydora | ................. | B01J 31/2239 585/511 |
| 2015/0119540 A1 * | 4/2015 | Holtcamp | ................. | C08F 4/02 526/130 |

FOREIGN PATENT DOCUMENTS

| | | | |
|---|---|---|---|
| JP | 9-194526 | * | 7/1997 |
| JP | 10-306116 | * | 11/1998 |
| KR | 10-2010-0060481 A | | 6/2010 |
| KR | 10-2011-0041498 A | | 4/2011 |
| KR | 10-2012-0102641 A | | 9/2012 |
| KR | 10-2013-0078965 A | | 7/2013 |
| WO | 2010/040741 A1 | | 4/2010 |

OTHER PUBLICATIONS

Kopf-Maier, Petra, et al., "Transition and Main-Group Metal Cyclopentadienyl Complexes: Preclinical Studies on a Series of Antitumor Agents of Different Structural Type". Bioinorganic Chemistry. Structure and Bonding, vol. 70. Springer, Berlin, Heidelberg (1988), pp. 103-185.*
Alt, Helmut G., et al., "Effect of the Nature of Metallocene Complexes of Group IV Metals on Their Performance in Catalytic Ethylene and Propylene Polymerization". Chem. Rev. 2000, 100, 1205-1221.*
McKnight, Andrew L., et al., "Group 4 ansa-Cyclopentadienyl-Amido Catalysts for Olefin Polymerization". Chem. Rev. 1998, 98, 2587-2598.*
Wilkinson, G., et al., "Bis-cyclopentadienyl Compounds of Ti, Zr, V, Nb and Ta". J. Am. Chem. Soc. 1954, 76, 17, 4281-4284.*

(Continued)

*Primary Examiner* — Bret P Chen
(74) *Attorney, Agent, or Firm* — Hamre, Schumann, Mueller & Larson, P.C.

(57) ABSTRACT

The present disclosure relates to a novel Group 5 metal compound, a method for preparing the Group 5 metal compound, a precursor composition for depositing a Group 5 metal-containing layer containing the Group 5 metal compound, and a method for depositing a Group 5 metal-containing layer using the precursor composition for depositing a Group 5 metal-containing layer.

12 Claims, 13 Drawing Sheets

(56) References Cited

OTHER PUBLICATIONS

Fedin, É.I., et al., J Struct Chem (1970) 11: 169-186. https://doi.org/10.1007/BF00743937.*
Budzelaar, Peter H.M., et al., "Trends in Cyclopentadienyl-Main-Group-Metal Bonding". Organometallics 2003, 22, 1562-1576.*
International Search Report of PCT/KR2017/009188 dated Nov. 30, 2017, 2 pages.
Wolfgang A. Herrmann et al., "First amido-functionalized niobium and tantalum complexes of the ansa-structural type: synthesis and photochemical Si—N bond cleavage," Journal of Organometallic Chemistry, Jan. 1996, vol. 506, pp. 357-361.

* cited by examiner

GROUP 5 METAL COMPOUND, METHOD FOR PREPARING THE SAME, PRECURSOR COMPOSITION FOR DEPOSITING LAYER CONTAINING THE SAME, AND METHOD FOR DEPOSITING LAYER USING THE SAME

CROSS-REFERENCE TO RELATED APPLICATION

This Application is a Continuation Application of PCT Application Ser. No. PCT/KR2017/009188 filed on Aug. 23, 2017, which claims the benefit of Korean Patent Application No. 10-2016-0115708 filed on Sep. 8, 2016. The disclosures of both applications are hereby incorporated herein by reference in their entireties.

TECHNICAL FIELD

The present disclosure relates to a novel Group 5 metal compound, a method for preparing the Group 5 metal compound, a precursor composition for depositing a Group 5 metal-containing layer containing the Group 5 metal compound, and a method for depositing a Group 5 metal-containing layer using the precursor composition for depositing a Group 5 metal-containing layer.

BACKGROUND

A metal layer of Group 5 metal, particularly tantalum (Ta) and niobium (Nb), and an oxide layer or nitride layer of tantalum and niobium can be used for manufacturing semiconductor devices. Particularly, a method of forming a tantalum-containing layer by sputtering has been used in manufacturing process of semiconductor devices. However, in order to form an extremely thin (several nm thick) tantalum-containing layer such as a copper diffusion barrier on an uneven surface, a chemical deposition method with excellent step coverage, particularly an atomic layer deposition method, is needed, and, thus, a Group 5 metal precursor compound suitable therefor is needed.

Pentakis(dimethylamido)tantalum (PDMAT), (tert-butyl-imido)tris(diethylamido)tantalum (TBTDET), (tert-butyl-imido)tris(diethylamido)niobium (TBTDEN), etc. have been known as organic metal precursor compounds capable of forming Group 5 metal-containing layers (see U.S. Pat. No. 6,552,209) However, PDMAT is solid and thus inconvenient for use in the chemical deposition method or the atomic layer deposition method. A liquid source is advantageous for use in the chemical deposition method or the atomic layer deposition method. A direct liquid injection (DLI) system configured to vaporize a liquid in a cylindrical container or vaporize a liquid injected at a constant flow rate has been widely used in manufacturing process of semiconductor devices. However, the rate of sublimation of a solid is proportional to the surface area of the solid which continues to change during sublimation, and, thus, it is difficult to regularly vaporize and supply the solid and a special device is needed. Further, all of PDMAT, TBTDET, and TBTDEN are poor in thermal stability and thus disadvantageous for use at high temperature. For example, it is difficult to use the compounds in the atomic layer deposition method for forming a uniform-thickness oxide layer on an uneven surface at 300° C. Accordingly, there is a need for a novel Group 5 metal precursor compound which can be used in commercial manufacturing process of semiconductor devices and has high thermal stability and is in a liquid state or viscous solid state at room temperature.

DISCLOSURE OF THE INVENTION

Problems to be Solved by the Invention

The present disclosure is conceived to provide a novel Group 5 metal compound, a method for preparing the Group 5 metal compound, a precursor composition for depositing a Group 5 metal-containing layer containing the Group 5 metal compound, and a method for depositing a Group 5 metal-containing layer using the precursor composition for depositing a Group 5 metal-containing layer.

However, problems to be solved by the present disclosure are not limited to the above-described problems. Although not described herein, other problems to be solved by the present disclosure can be clearly understood by those skilled in the art from the following description.

Means for Solving the Problems

According to a first aspect of the present disclosure, there is provided a Group 5 metal compound, represented by the following Chemical Formula 1:

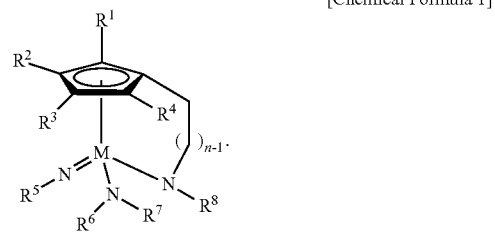

[Chemical Formula 1]

In the above Chemical Formula 1, M is Ta or Nb; each of $R^1$, $R^2$, $R^3$, and $R^4$ is independently hydrogen, or a linear or branched $C_{1-4}$ alkyl group; $R^5$ is a linear or branched $C_{3-6}$ alkyl group; each of $R^6$, $R^7$ and $R^8$ is independently a linear or branched $C_{1-4}$ alkyl group; and n is an integer of from 1 to 4.

According to a second aspect of the present disclosure, there is provided a method for preparing a Group 5 metal compound represented by the following Chemical Formula 1, which includes reacting a compound $(R^5N=)M(NR^6R^7)_3$ represented by the following Chemical Formula 2 with a compound $R^1R^2R^3R^4Cp(CH_2)_nNHR^8$ represented by the following Chemical Formula 3:

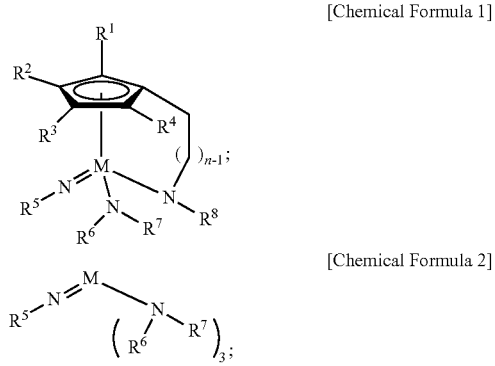

[Chemical Formula 1]

[Chemical Formula 2]

[Chemical Formula 3]

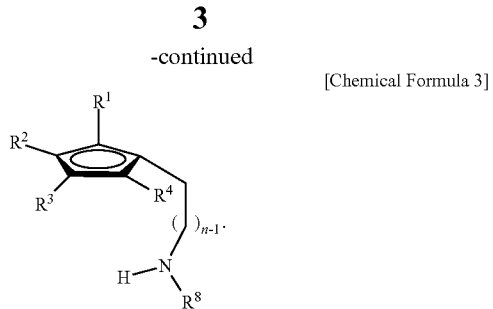

In each of the above Formulas 1 to 3, M is Ta or Nb; each of $R^1$, $R^2$, $R^3$, and $R^4$ is independently hydrogen, or a linear or branched $C_{1-4}$ alkyl group; $R^5$ is a linear or branched $C_{3-6}$ alkyl group; each of $R^6$, $R^7$ and $R^8$ is independently a linear or branched $C_{1-4}$ alkyl group; and n is an integer of from 1 to 4.

According to a third aspect of the present disclosure, there is provided a precursor composition for depositing a Group 5 metal-containing layer, including the Group 5 metal compound according to the first aspect of the present disclosure.

According to a fourth aspect of the present disclosure, there is provided a method for depositing a Group 5 metal-containing layer, including forming a Group 5 metal-containing layer on a substrate using the precursor composition for depositing a Group 5 metal-containing layer of the third aspect of the present disclosure.

Effects of the Invention

The novel Group 5 metal compound according to exemplary embodiments of the present disclosure can be formed to a liquid state or viscous solid state at room temperate and thus has improved thermal stability and high volatility.

The novel Group 5 metal element-containing compound according to exemplary embodiments of the present disclosure has high thermal stability and thus can be used as a precursor for atomic layer deposition (ALD) or chemical vapor deposition (CVD) to form a high-quality Group 5 metal-containing layer and particularly can be used to uniformly form a Group 5 metal-containing layer having a small and uniform thickness on a substrate having unevenness (corrugations) on its surface. Accordingly, the method for forming a Group 5 metal-containing layer according to exemplary embodiments of the present disclosure can be applied to commercial manufacturing of semiconductor devices.

The novel Group 5 metal compound according to exemplary embodiments of the present disclosure can be used as a precursor for ALD, CVD, and the like and thus can provide performance, e.g., improved thermal stability, high volatility or increased deposition rate, required for manufacturing of next-generation devices such as semiconductors and therefore can be usefully used for forming a Group 5 metal-containing layer or thin film.

BEST MODE FOR CARRYING OUT THE INVENTION

Figure 1:
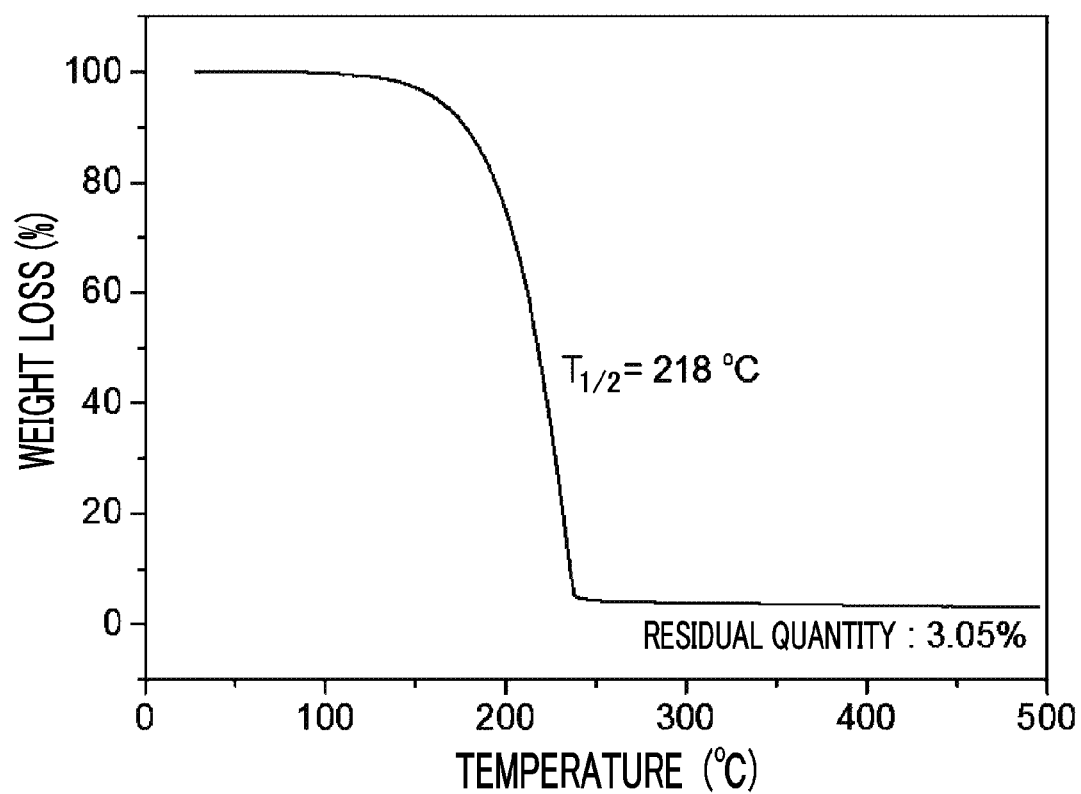
FIG. 1 is a graph showing a result of thermogravimetry analysis (TGA) on $(Cp(CH_2)_2N(CH_3))(^tBuN)Ta(NEt_2)$ in accordance with an example of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl" includes linear or branched alkyl groups having 1 to 12 carbon atoms, 1 to 10 carbon atoms, 1 to 8 carbon atoms, 1 to 5 carbon atoms, 1 to 3 carbon atoms, 3 to 8 carbon atoms, or 3 to 5 carbon atoms. For example, the alkyl group may include methyl group, ethyl group, n-propyl group ($^n$Pr), iso-propyl group ($^i$Pr), n-butyl group ($^n$Bu), tert-butyl group ($^t$Bu), iso-butyl group ($^i$Bu), sec-butyl group ($^s$Bu), n-pentyl group, tert-pentyl group, iso-pentyl group, sec-pentyl group, neo-pentyl group, 3-pentyl group, hexyl group, iso-hexyl group, heptyl group, 4,4-dimethyl pentyl group, octyl group, 2,2,4-trimethyl pentyl group, nonyl group, decyl group, undecyl group, dodecyl group, and isomers thereof, but may not be limited thereto.

Through the whole document, the term "layer" may include "layer" or "thin film", but may not be limited thereto.

Hereafter, exemplary embodiments and examples of the present disclosure will be described in detail with reference to the accompanying drawings, but the present disclosure may not be limited to the following exemplary embodiments, examples and drawings.

According to a first aspect of the present disclosure, there is provided a Group 5 metal compound, represented by the following Chemical Formula 1:

[Chemical Formula 1]

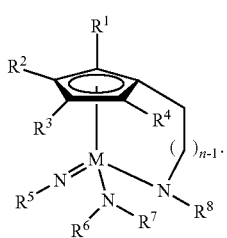

In the above Chemical Formula 1, M is Ta or Nb; each of $R^1$, $R^2$, $R^3$, and $R^4$ is independently hydrogen, or a linear or branched $C_{1-4}$ alkyl group; $R^5$ is a linear or branched $C_{3-6}$ alkyl group; each of $R^6$, $R^7$ and $R^8$ is independently a linear or branched $C_{1-4}$ alkyl group; and n is an integer of from 1 to 4.

In an embodiment of the present disclosure, $R^1$, $R^2$, $R^3$, and $R^4$ may be identical to or different from each other, and may include, for example, hydrogen (H), methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^1$, $R^2$, $R^3$, and $R^4$ may be independently hydrogen (H), methyl group, or ethyl group, but may not be limited thereto.

In an embodiment of the present disclosure, $R^5$ may be n-propyl group, iso-propyl group, n-butyl group, tert-butyl group, iso-butyl group, sec-butyl group, n-pentyl group, tert-pentyl group, iso-pentyl group, sec-pentyl group, neopentyl group, or 3-pentyl group, but may not be limited thereto.

In an embodiment of the present disclosure, $R^6$, $R^7$, and $R^8$ may be identical to or different from each other, and may include, for example, methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^6$, $R^7$, and $R^8$ may be independently methyl group or ethyl group, but may not be limited thereto.

In an embodiment of the present disclosure, the Group 5 metal compound may include a compound selected from the following compounds, but may not be limited thereto:

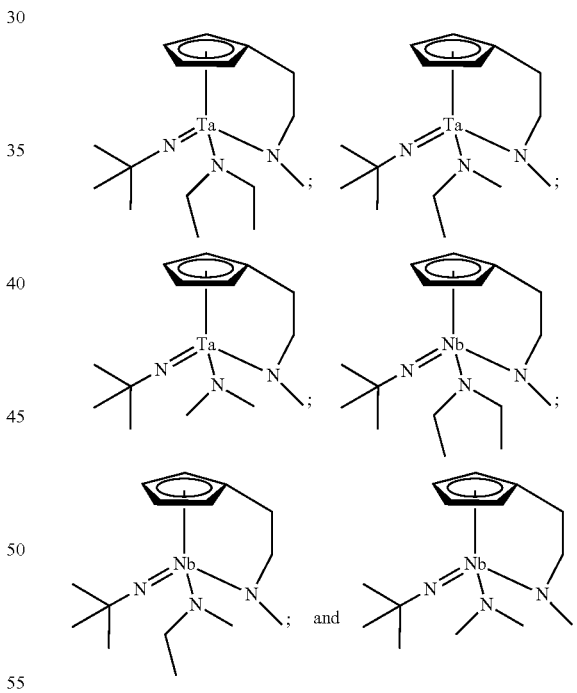

In an embodiment of the present disclosure, the Group 5 metal compound may be in a liquid state or viscous solid state at room temperature.

According to a second aspect of the present disclosure, there is provided a method for preparing a Group 5 metal compound represented by the following Chemical Formula 1, which includes reacting a compound $(R^5N=)M(NR^6R^7)_3$ represented by the following Chemical Formula 2 with a compound $R^1R^2R^3R^4Cp(CH_2)_nNHR^8$ represented by the following Chemical Formula 3:

[Chemical Formula 1]

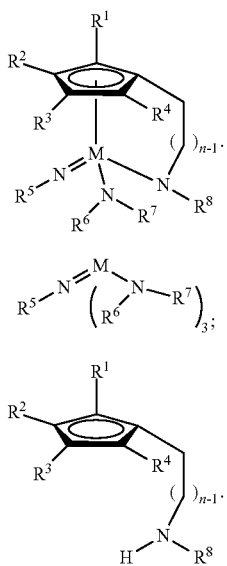

[Chemical Formula 2]

[Chemical Formula 3]

In each of the above Formulas 1 to 3, M is Ta or Nb; each of $R^1$, $R^2$, $R^3$, and $R^4$ is independently hydrogen, or a linear or branched $C_{1-4}$ alkyl group; $R^5$ is a linear or branched $C_{3-6}$ alkyl group; each of $R^6$, $R^7$ and $R^8$ is independently a linear or branched $C_{1-4}$ alkyl group; and n is an integer of from 1 to 4.

In an embodiment of the present disclosure, $R^1$, $R^2$, $R^3$, and $R^4$ may be identical to or different from each other, and may include, for example, hydrogen (H), methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^1$, $R^2$, $R^3$, and $R^4$ may be independently hydrogen (H), methyl group, or ethyl group, but may not be limited thereto.

In an embodiment of the present disclosure, $R^5$ may be n-propyl group, isopropyl group, n-butyl group, tert-butyl group, iso-butyl group, sec-butyl group, n-pentyl group, tert-pentyl group, iso-pentyl group, sec-pentyl group, neopentyl group, or 3-pentyl group, but may not be limited thereto.

In an embodiment of the present disclosure, $R^6$, $R^7$, and $R^8$ may be identical to or different from each other, and may include, for example, methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^6$, $R^7$, and $R^8$ may be independently methyl group or ethyl group, but may not be limited thereto.

In an embodiment of the present disclosure, the Group 5 metal compound may include a compound selected from the following compounds, but may not be limited thereto:

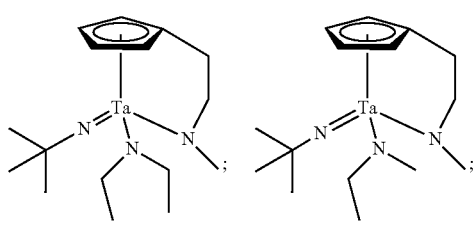

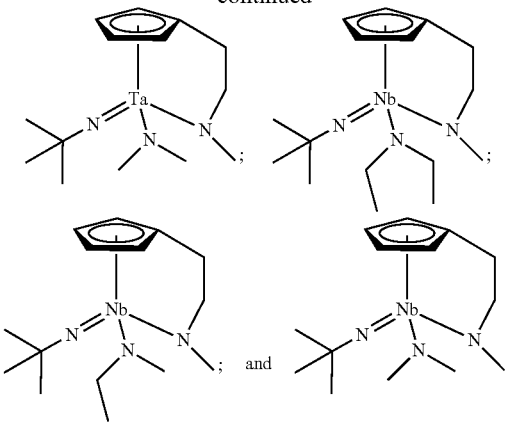

-continued

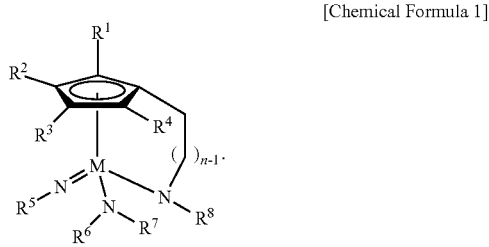

In an embodiment of the present disclosure, the Group 5 metal compound may be in a liquid state or viscous solid state at room temperature.

In an embodiment of the present disclosure, the reaction may be carried out at room temperature, but may not be limited thereto.

According to a third aspect of the present disclosure, there is provided a precursor composition for depositing a Group 5 metal-containing layer, including the Group 5 metal compound according to the first aspect of the present disclosure.

The Group 5 metal compound according to the first aspect of the present disclosure is a Group 5 metal compound, represented by the following Chemical Formula 1, and in the Chemical Formula 1, M is Ta or Nb; each of $R^1$, $R^2$, $R^3$, and $R^4$ is independently hydrogen, or a linear or branched $C_{1-4}$ alkyl group; $R^5$ is a linear or branched $C_{3-6}$ alkyl group; each of $R^6$, $R^7$ and $R^8$ is independently a linear or branched $C_{1-4}$ alkyl group; and n is an integer of from 1 to 4:

[Chemical Formula 1]

In an embodiment of the present disclosure, $R^1$, $R^2$, $R^3$, and $R^4$ may be identical to or different from each other, and may include, for example, hydrogen (H), methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^1$, $R^2$, $R^3$, and $R^4$ may be independently hydrogen (H), methyl group, or ethyl group, but may not be limited thereto.

In an embodiment of the present disclosure, $R^5$ may be n-propyl group, iso-propyl group, n-butyl group, tert-butyl group, iso-butyl group, sec-butyl group, n-pentyl group, tert-pentyl group, iso-pentyl group, sec-pentyl group, neopentyl group, or 3-pentyl group, but may not be limited thereto.

In an embodiment of the present disclosure, $R^6$, $R^7$, and $R^8$ may be identical to or different from each other, and may include, for example, methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^6$, $R^7$, and $R^8$ may be independently methyl group or ethyl group, but may not be limited thereto.

In an embodiment of the present disclosure, the Group 5 metal compound may include a compound selected from the following compounds, but may not be limited thereto:

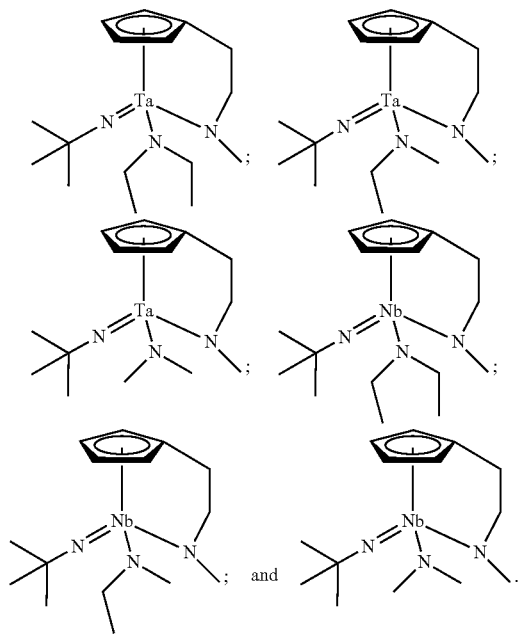

In an embodiment of the present disclosure, the Group 5 metal compound may be in a liquid state or viscous solid state at room temperature.

In an embodiment of the present disclosure, the Group 5 metal-containing layer may be a tantalum-containing layer or thin film or a niobium-containing layer or thin film, and more specifically, a tantalum metal layer or thin film, a tantalum oxide layer or thin film, a tantalum nitride layer or thin film, a niobium metal layer or thin film, a niobium oxide layer or thin film, or a niobium nitride layer or thin film, but may not be limited thereto.

In an embodiment of the present disclosure, the Group 5 metal-containing layer may be a thin film having a nanometer-scale thickness of, e.g., from about 1 nm to about 100 nm, from about 1 nm to about 80 nm, from about 1 nm to about 60 nm, from about 1 nm to about 40 nm, from about 1 nm to about 20 nm, from about 1 nm to about 10 nm, from about 1 nm to about 5 nm, from about 5 nm to about 100 nm, from about 10 nm to about 100 nm, from about 30 nm to about 100 nm, from about 40 nm to about 100 nm, from about 60 nm to about 100 nm, or from about 80 nm to about 100 nm, but may not be limited thereto.

According to a fourth aspect of the present disclosure, there is provided a method for depositing a Group 5 metal-containing layer, including forming a Group 5 metal-containing layer on a substrate using the precursor composition for depositing a Group 5 metal-containing layer of the third aspect of the present disclosure.

The precursor composition for depositing a Group 5 metal-containing layer of the third aspect of the present disclosure includes the Group 5 metal compound of the first aspect of the present disclosure, and the Group 5 metal compound according to the first aspect of the present disclosure is a Group 5 metal compound, represented by the following Chemical Formula 1, and in the Chemical Formula 1, M is Ta or Nb; each of $R^1$, $R^2$, $R^3$, and $R^4$ is independently hydrogen, or a linear or branched $C_{1-4}$ alkyl group; $R^5$ is a linear or branched $C_{3-6}$ alkyl group; each of $R^6$, $R^7$ and $R^8$ is independently a linear or branched $C_{1-4}$ alkyl group; and n is an integer of from 1 to 4:

[Chemical Formula 1]

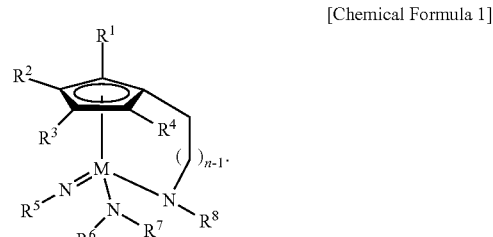

In an embodiment of the present disclosure, $R^1$, $R^2$, $R^3$, and $R^4$ may be identical to or different from each other, and may include, for example, hydrogen (H), methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^1$, $R^2$, $R^3$, and $R^4$ may be independently hydrogen (H), methyl group, or ethyl group, but may not be limited thereto.

In an embodiment of the present disclosure, $R^5$ may be n-propyl group, iso-propyl group, n-butyl group, tert-butyl group, iso-butyl group, sec-butyl group, n-pentyl group, tert-pentyl group, iso-pentyl group, sec-pentyl group, neopentyl group, or 3-pentyl group, but may not be limited thereto.

In an embodiment of the present disclosure, $R^6$, $R^7$, and $R^8$ may be identical to or different from each other, and may include, for example, methyl group, ethyl group, n-propyl group, iso-propyl group, n-butyl group, iso-butyl group, tert-butyl group, sec-butyl group, or isomers thereof, but may not be limited thereto.

In an embodiment of the present disclosure, each of $R^6$, $R^7$, and $R^8$ may be independently methyl group or ethyl group, but may not be limited thereto.

In an embodiment of the present disclosure, the Group 5 metal compound may include a compound selected from the following compounds, but may not be limited thereto:

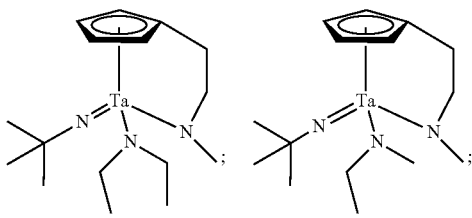

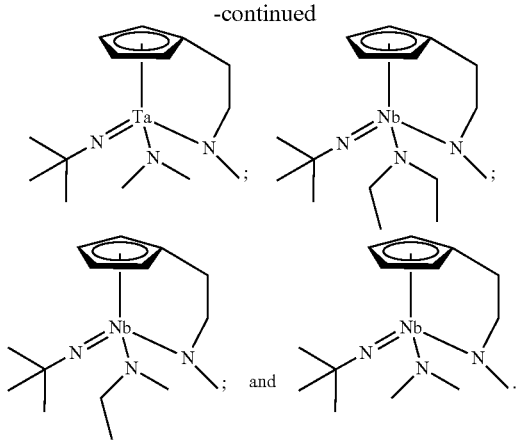

In an embodiment of the present disclosure, the Group 5 metal compound may be in a liquid state or viscous solid state at room temperature.

In an embodiment of the present disclosure, the Group 5 metal-containing layer may be a tantalum-containing layer or thin film or a niobium-containing layer or thin film, and more specifically, a tantalum metal layer or thin film, a tantalum oxide layer or thin film, a tantalum nitride layer or thin film, a niobium metal layer or thin film, a niobium oxide layer or thin film, or a niobium nitride layer or thin film, but may not be limited thereto.

In an embodiment of the present disclosure, the Group 5 metal-containing layer may be a thin film having a nanometer-scale thickness of, e.g., from about 1 nm to about 100 nm, from about 1 nm to about 80 nm, from about 1 nm to about 60 nm, from about 1 nm to about 40 nm, from about 1 nm to about 20 nm, from about 1 nm to about 10 nm, from about 1 nm to about 5 nm, from about 5 nm to about 100 nm, from about 10 nm to about 100 nm, from about 30 nm to about 100 nm, from about 40 nm to about 100 nm, from about 60 nm to about 100 nm, or from about 80 nm to about 100 nm, but may not be limited thereto.

In an embodiment of the present disclosure, the substrate may include unevenness (corrugations) formed on the surface thereof, but may not be limited thereto. For example, the substrate may be a substrate including micro unevenness (corrugation) with an aspect ratio of about 1 or more and a width of about 1 μm or less, but may not be limited thereto. For example, the unevenness (corrugation) may have an aspect of about 1 or more, about 1.5 or more, about 2 or more, about 2.5 or more, about 3 or more, about 3.5 or more, about 4 or more, about 4.5 or more, about 5 or more, about 5.5 or more, about 6 or more, about 6.5 or more, about 7 or more, about 7.5 or more, about 8 or more, about 8.5 or more, about 9 or more, about 9.5 or more, or about 10 or more, but may not be limited thereto. For example, the unevenness (corrugation) may have a width of about 1 μm or less, about 0.9 μm or less, about 0.8 μm or less, about 0.7 μm or less, about 0.6 μm or less, about 0.5 μm or less, about 0.4 μm or less, about 0.3 μm or less, about 0.2 μm or less, or about 0.1 μm or less, but may not be limited thereto.

In an embodiment of the present disclosure, the method for depositing a Group 5 metal-containing layer or thin film may include supplying the precursor composition for depositing a Group 5 metal-containing layer to the surface of the substrate located within a deposition chamber and forming a Group 5 metal-containing layer or thin film, but may not be limited thereto. For example, the precursor composition for depositing a Group 5 metal-containing layer may be transferred in a vapor phase onto the substrate within the deposition chamber by a bubbling method, vapor phase mass flow controller (MFC) method, a direct liquid injection (DLI) method, or a liquid delivery system (LDS) for delivering the precursor composition for depositing a Group 5 metal-containing layer while dissolving it in an organic solvent, but may not be limited thereto. For example, a carrier gas or purge gas for transferring the precursor composition for depositing a Group 5 metal-containing layer onto the substrate within the deposition chamber may include a gas selected from the group consisting of argon, helium, nitrogen, and combinations thereof, but may not be limited thereto. The method for depositing a layer may employ any method and device known in the art and may be performed using an additional reactant gas as necessary, but may not be limited thereto.

In an embodiment of the present disclosure, the Group 5 metal-containing layer may be deposited by chemical vapor deposition or atomic layer deposition, but may not be limited thereto. For example, the method for depositing a Group 5 metal-containing layer or thin film may be performed by chemical vapor deposition (CVD), metal organic chemical vapor deposition (MOCVD) or atomic layer deposition (ALD), and the chemical vapor deposition (CVD), metal organic chemical vapor deposition (MOCVD) or atomic layer deposition (ALD) may be performed using a deposition apparatus, deposition conditions, and additional reaction gases known in the art, but may not be limited thereto.

In an embodiment of the present disclosure, the Group 5 metal-containing layer may include a Group 5 metal oxide-containing layer, and a reactant gas for depositing the Group 5 metal oxide-containing layer may include a reactant gas containing an O-containing material selected from the group consisting of water vapor ($H_2O$), oxygen ($O_2$), ozone ($O_3$), and combinations thereof, but may not be limited thereto.

In an embodiment of the present disclosure, the Group 5 metal-containing layer may include a Group 5 metal nitride-containing layer, and a reactant gas for depositing the Group 5 metal nitride-containing layer may include a reactant gas containing an N-containing material selected from the group consisting of ammonia ($NH_3$), hydrazine, dimethylhydrazine, and combinations thereof, but may not be limited thereto.

In an embodiment of the present disclosure, the Group 5 metal-containing layer may be deposited at a temperature in the range of from room temperature to about 700° C., or from about 50° C. to about 700° C., but may not be limited thereto. For example, the deposition temperature may be from room temperature to about 700° C., from about 50° C. to about 700° C., from about 50° C. to about 600° C., from about 50° C. to about 500° C., from about 50° C. to about 400° C., from about 50° C. to about 300° C., from about 80° C. to about 700° C., from about 100° C. to about 700° C., from about 200° C. to about 700° C., from about 300° C. to about 700° C., from about 400° C. to about 700° C., from about 500° C. to about 700° C., from about 600° C. to about 700° C., or from about 100° C. to about 700° C., from about 100° C. to about 600° C., from about 100° C. to about 500° C., from about 100° C. to about 400° C., from about 100° C. to about 300° C., from about 150° C. to about 700° C., from about 150° C. to about 600° C., from about 150° C. to about 500° C., from about 150° C. to about 400° C., or from about 150° C. to about 300° C., but may not be limited thereto.

Hereinafter, the present disclosure will be explained in more detail with reference to Examples. However, the following Examples are illustrative only for better understanding of the present disclosure but do not limit the present disclosure.

MODE FOR CARRYING OUT THE INVENTION

Examples

<Example 1> Preparation of (Cp(CH$_2$)$_2$N(CH$_3$))($^t$BuN)Ta(NEt$_2$)

Figure 2:
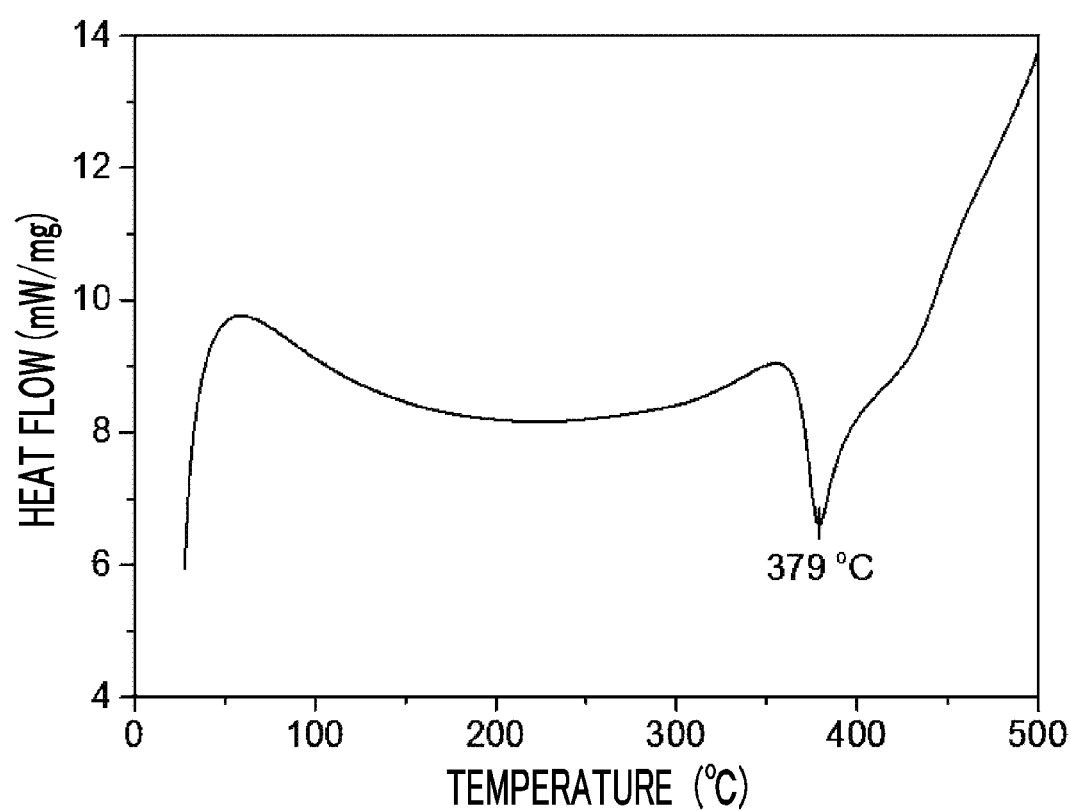
FIG. 2 is a graph showing a result of differential scanning calorimetry (DSC) on $(Cp(CH_2)_2N(CH_3))(^tBuN)Ta(NEt_2)$ in accordance with an example of the present disclosure.

29 g (0.062 mol, 1 equivalent) of tris(diethylamido)(tert-butylimido)tantalum [($^t$BuN)Ta(NEt$_2$)$_3$)] and 150 mL of toluene were put into a flame-dried 500 mL Schlenk flask and then stirred at room temperature. After 7.6 g (0.062 mol, 1 equivalent) cyclopentadienylethylmethylamine [Cp(CH$_2$)$_2$NH(CH$_3$)] was dropwisely added to the flask at room temperature, the temperature of the reaction solution was raised to 60° C. and then the reaction solution was stirred for 4 hours. The solvent was removed from the reaction solution under reduced pressure and distillation was performed under reduced pressure to obtain 19 g (yield of 69%) of a pale yellow liquid compound represented by the following Compound 1. Results of thermogravimetry analysis (TGA) and differential scanning calorimetry (DSC) on the compound represented by the following Compound 1 were as shown in FIG. 1 and FIG. 2, respectively.

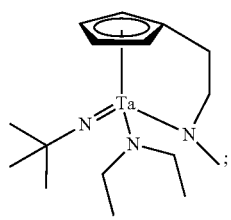

<Compound 1>

Boiling point (bp): 110° C. (0.4 torr);
Elemental analysis calcd for (C$_{16}$H$_{30}$N$_3$Ta): C, 43.15, H, 6.79, N, 9.43; found C, 42.99, H, 6.81, N, 9.49;
$^1$H-NMR (400 MHz, C$_6$D$_6$, 25° C.) δ 5.967, 5.839, 5.702, 5.654 (m, 4H, C$_5$H$_4$(CH$_2$)$_2$N(CH$_3$)), δ 4.275, 3.687, 2.434, 2.361 (m, 4H, C$_5$H$_4$(CH$_2$)$_2$N(CH$_3$)), δ 3.536 (m, 4H, N(CH$_2$CH$_3$)$_2$), δ 3.389 (s, 3H C$_5$H$_4$(CH$_2$)$_2$N(CH$_3$)), δ 1.312 (s, 9H, NC(CH$_3$)$_3$), δ 1.126 (t, 6H, N(CH$_2$CH$_3$)$_2$).

<Example 2> Preparation of (Cp(CH$_2$)$_2$N(CH$_3$))($^t$BuN)Ta(NEtMe)

Figure 3:
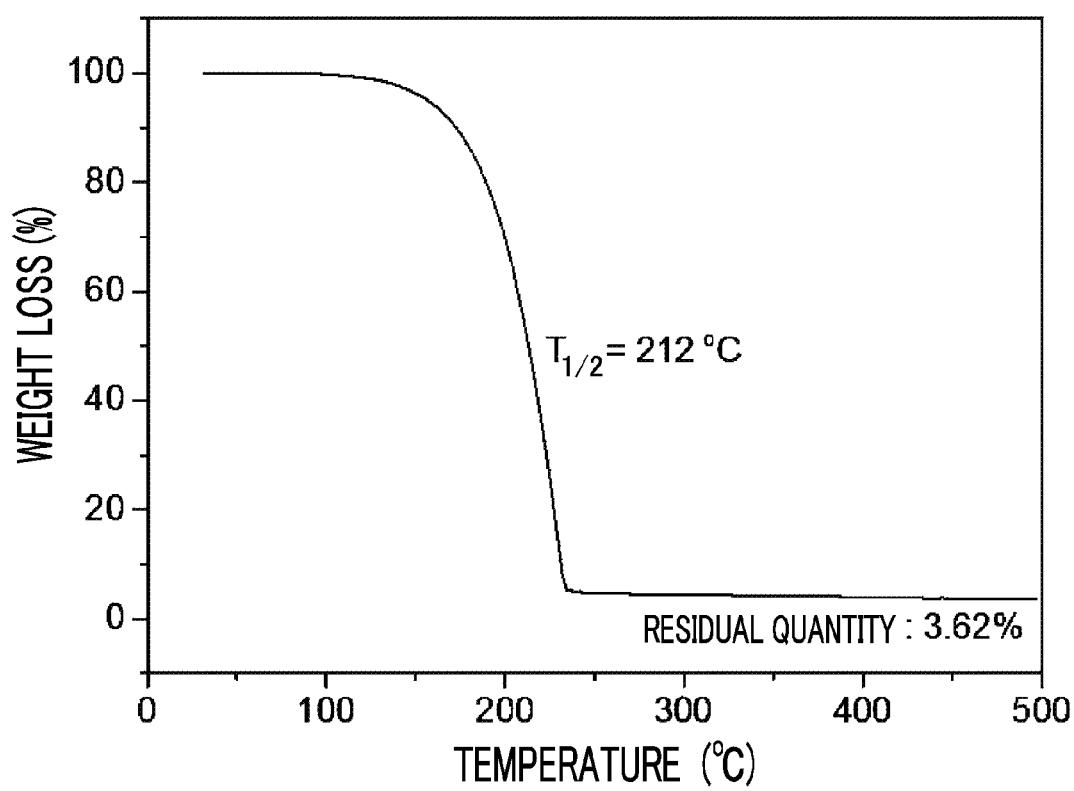
FIG. 3 is a graph showing a result of thermogravimetry analysis (TGA) on $(Cp(CH_2)_2N(CH_3))(^tBuN)Ta(NEtMe)$ in accordance with an example of the present disclosure.
Figure 4:
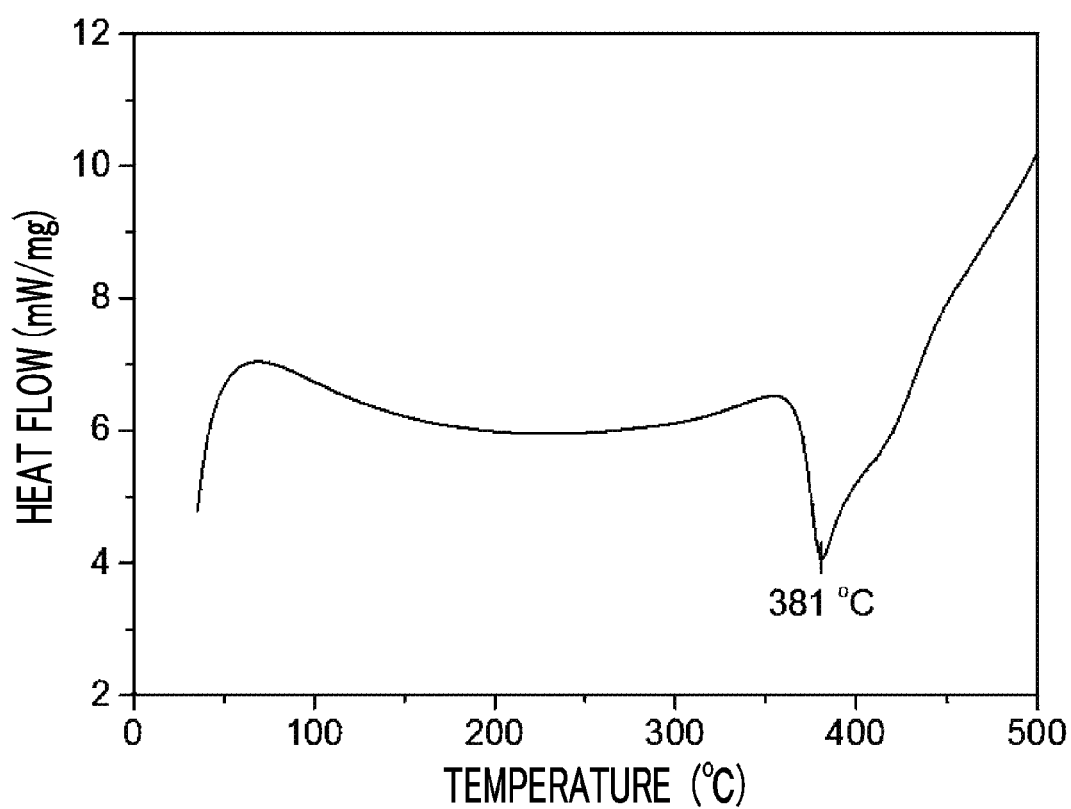
FIG. 4 is a graph showing a result of differential scanning calorimetry (DSC) on $(Cp(CH_2)_2N(CH_3))(^tBuN)Ta(NEtMe)$ in accordance with an example of the present disclosure.

100 g (0.235 mol, 1 equivalent) of tris(ethylmethylamido)(tert-butylimido)tantalum [($^t$BuN)Ta(NEtMe)$_3$)] and 300 mL of toluene were put into a flame-dried 1 L Schlenk flask and then stirred at room temperature. After 28.7 g (0.235 mol, 1 equivalent) cyclopentadienylethylmethylamine [Cp(CH$_2$)$_2$NH(CH$_3$)] was dropwisely added to the flask at room temperature, the temperature of the reaction solution was raised to 60° C. and then the reaction solution was stirred for 4 hours. The solvent was removed from the reaction solution under reduced pressure and distillation was performed under reduced pressure to obtain 66 g (yield of 65%) of a pale yellow liquid compound represented by the following Compound 2. Results of thermogravimetry analysis (TGA) and differential scanning calorimetry (DSC) on the compound represented by the following Compound 2 were as shown in FIG. 3 and FIG. 4, respectively.

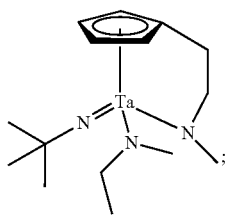

<Compound 2>

Boiling point (bp): 108° C. (0.4 torr);
Elemental analysis calcd for (C$_{15}$H$_{28}$N$_3$Ta): C, 41.77, H, 6.54, N, 9.74; found C, 41.39, H, 6.61, N, 9.69;
$^1$H-NMR (400 MHz, C$_6$D$_6$, 25° C.) δ 5.977, 5.832, 5.734, 5.632 (m, 4H, C$_5$H$_4$(CH$_2$)$_2$N(CH$_3$)), δ 4.249, 3.704, 2.441, 2.358 (m, 4H, C$_5$H$_4$(CH$_2$)$_2$N(CH$_3$)), δ 3.645 (m, 2H, N(CH$_2$CH$_3$)(CH$_3$)), δ 3.407 (s, 3H, C$_5$H$_4$(CH$_2$)$_2$N(CH$_3$)), δ 3.260 (s, 3H, N(CH$_2$CH$_3$)(CH$_3$)), δ 1.315 (s, 9H, NC(CH$_3$)$_3$), δ 1.156 (t, 3H, N(CH$_2$CH$_3$)(CH$_3$)).

<Example 3> Preparation of (Cp(CH$_2$)$_2$N(CH$_3$))($^t$BuN)Ta(NMe$_2$)

Figure 5:
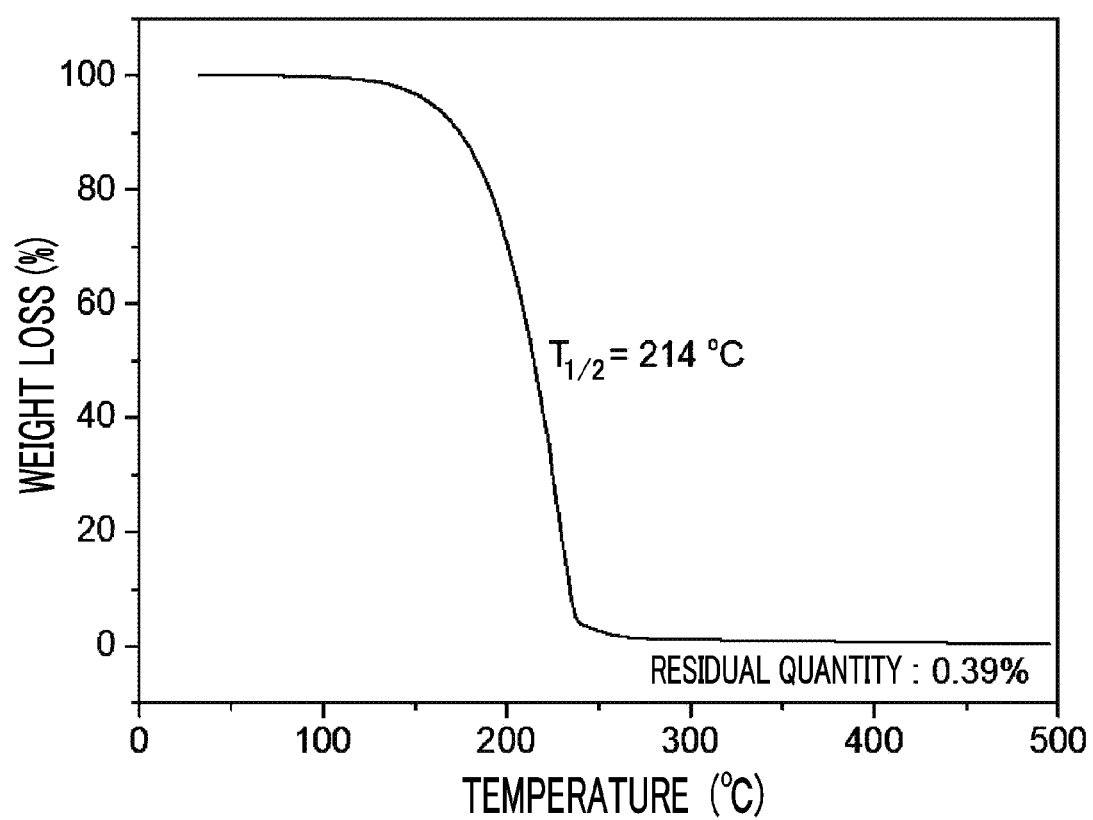
FIG. 5 is a graph showing a result of thermogravimetry analysis (TGA) on $(Cp(CH_2)_2N(CH_3))(^tBuN)Ta(NMe_2)$ in accordance with an example of the present disclosure.
Figure 6:
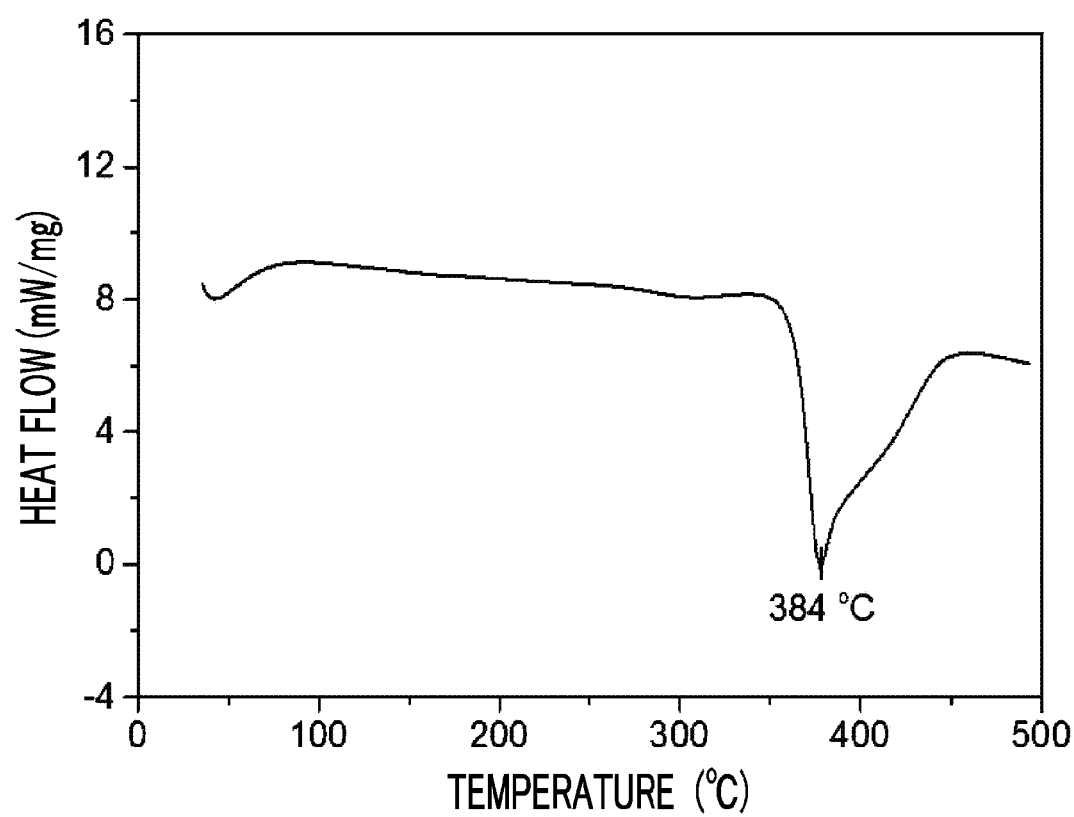
FIG. 6 is a graph showing a result of differential scanning calorimetry (DSC) on $(Cp(CH_2)_2N(CH_3))(^tBuN)Ta(NMe_2)$ in accordance with an example of the present disclosure.

100 g (0.260 mol, 1 equivalent) of tris(diethylamido)(tert-butylimido)tantalum [($^t$BuN)Ta(NMe$_2$)$_3$)] and 300 mL of toluene were put into a flame-dried 500 mL Schlenk flask and then stirred at room temperature. After 32.1 g (0.062 mol, 1 equivalent) cyclopentadienylethylmethylamine [Cp(CH$_2$)$_2$NH(CH$_3$)] was dropwisely added to the flask at room temperature, the temperature of the reaction solution was raised to 60° C. and then the reaction solution was stirred for 4 hours. The solvent was removed from the reaction solution under reduced pressure and distillation was performed under reduced pressure to obtain 77 g (yield of 71%) of a pale yellow liquid compound represented by the following Compound 3. Results of thermogravimetry analysis (TGA) and differential scanning calorimetry (DSC) on the compound represented by the following Compound 3 were as shown in FIG. 5 and FIG. 6, respectively.

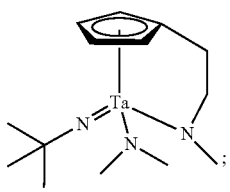

<Compound 3>

Boiling point (bp): 107° C. (0.4 torr);
Elemental analysis calcd for (C$_{14}$H$_{26}$N$_3$Ta): C, 40.29, H, 6.28, N, 10.07; found C, 40.39, H, 6.31, N, 10.03;
$^1$H-NMR (400 MHz, C$_6$D$_6$, 25° C.) δ 5.958, 5.826, 5.739, 5.598 (m, 4H, C$_5$H$_4$(CH$_2$)$_2$N(CH$_3$)), δ 4.273, 3.695, 2.450, 2.350 (m, 4H, C$_5$H$_4$(CH$_2$)$_2$N(CH$_3$)), δ 3.429 (s, 3H, C$_5$H$_4$(CH$_2$)$_2$N(CH$_3$)), δ 3.390 (s, 6H, N(CH$_3$)$_2$), δ 1.331 (S, 9H, NC(CH$_3$)$_3$).

<Example 4> Preparation of (Cp(CH$_2$)$_2$N(CH$_3$))($^t$BuN)Nb(NEt$_2$)

Figure 7:
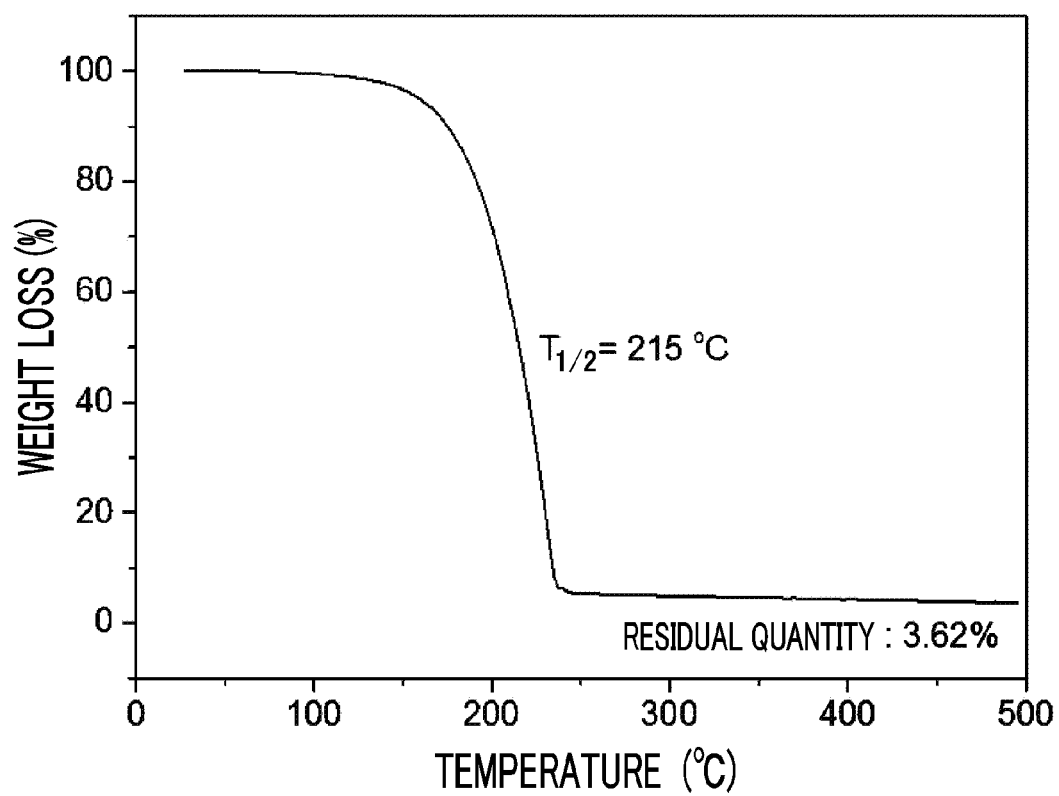
FIG. 7 is a graph showing a result of thermogravimetry analysis (TGA) on $(Cp(CH_2)_2N(CH_3))(^tBuN)Nb(NEt_2)$ in accordance with an example of the present disclosure.
Figure 8:
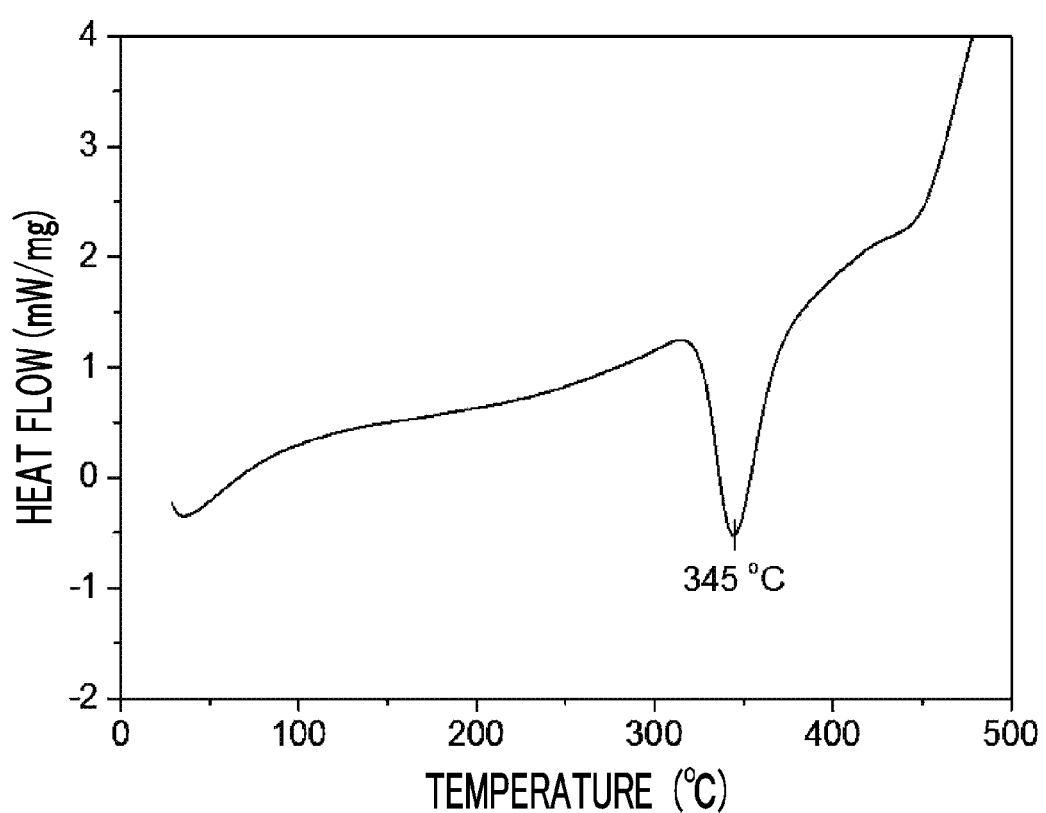
FIG. 8 is a graph showing a result of differential scanning calorimetry (DSC) on $(Cp(CH_2)_2N(CH_3))(^tBuN)Nb(NEt_2)$ in accordance with an example of the present disclosure.

100 g (0.263 mol, 1 equivalent) of tris(diethylamido)(tert-butylimido)tantalum [($^t$BuN)Nb(NEt$_2$)$_3$)] and 300 mL of toluene were put into a flame-dried 500 mL Schlenk flask and then stirred at room temperature. After 32.4 g (0.263 mol, 1 equivalent) cyclopentadienylethylmethylamine [Cp(CH$_2$)$_2$NH(CH$_3$)] was dropwisely added to the flask at room temperature, the temperature of the reaction solution was raised to 60° C. and then the reaction solution was stirred for 4 hours. The solvent was removed from the reaction solution under reduced pressure and distillation was performed under reduced pressure to obtain 64 g (yield of 68%) of a pale yellow liquid compound represented by the following Compound 4. Results of thermogravimetry analysis (TGA) and differential scanning calorimetry (DSC) on the compound represented by the following Compound 4 were as shown in FIG. 7 and FIG. 8, respectively.

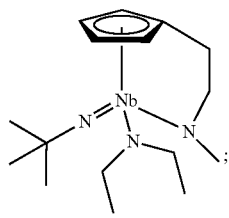

<Compound 4>

Boiling point (bp): 110° C. (0.4 torr);
Elemental analysis calcd for (C$_{16}$H$_{30}$N$_3$Nb): C, 53.78, H, 8.46, N, 11.76; found C, 53.65, H, 8.51, N, 11.81;
$^1$H-NMR (400 MHz, C$_6$D$_6$, 25° C.) δ 5.981, 5.813, 5.728, 5.698 (m, 4H, C$_5$H$_4$(CH$_2$)$_2$N(CH$_3$)), δ 4.134, 3.594, 2.508, 2.389 (m, 4H, C$_5$H$_4$(CH$_2$)$_2$N(CH$_3$)), δ 3.530 (m, 4H, N(CH$_2$CH$_3$)$_2$), δ 3.386 (s, 3H, C$_5$H$_4$(CH$_2$)$_2$N(CH$_3$)), δ 1.261 (s, 9H, NC(CH$_3$)$_3$), δ 1.133 (t, 6H, N(CH$_2$CH$_3$)$_2$).

<Example 5> Preparation of (Cp(CH$_2$)$_2$N(CH$_3$))($^t$BuN)Nb(NEtMe)

Figure 9:
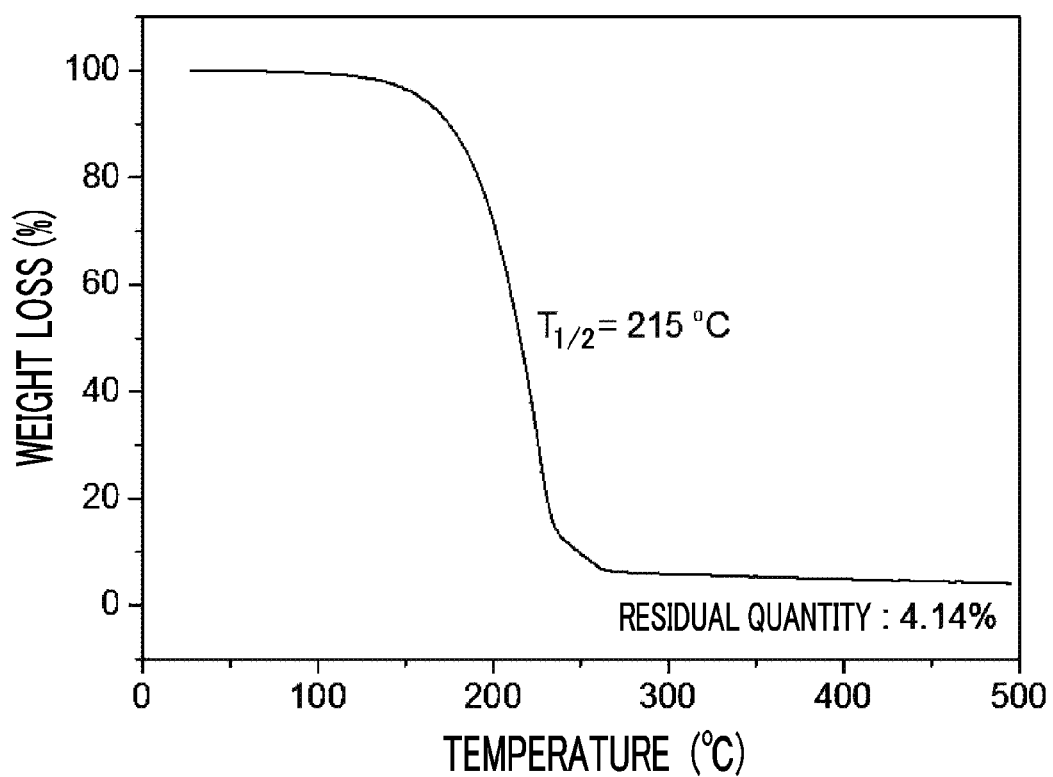
FIG. 9 is a graph showing a result of thermogravimetry analysis (TGA) on $(Cp(CH_2)_2N(CH_3))(^tBuN)Nb(NEtMe)$ in accordance with an example of the present disclosure.
Figure 10:
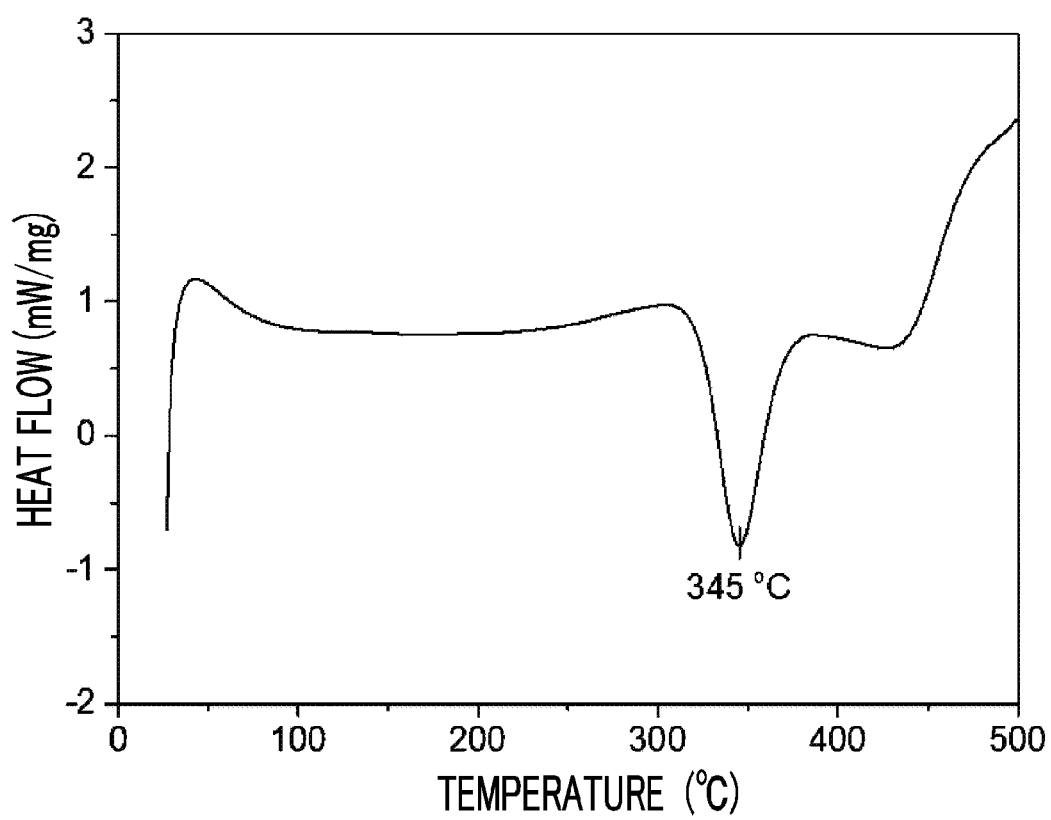
FIG. 10 is a graph showing a result of differential scanning calorimetry (DSC) on $(Cp(CH_2)_2N(CH_3))(^tBuN)Nb(NEtMe)$ in accordance with an example of the present disclosure.

100 g (0.296 mol, 1 equivalent) of tris(diethylamido)(tert-butylimido)tantalum [($^t$BuN)Nb(NEtMe)$_3$] and 300 mL of toluene were put into a flame-dried 500 mL Schlenk flask and then stirred at room temperature. After 36.4 g (0.296 mol, 1 equivalent) cyclopentadienylethylmethylamine [Cp(CH$_2$)$_2$NH(CH$_3$)] was dropwisely added to the flask at room temperature, the temperature of the reaction solution was raised to 60° C. and then the reaction solution was stirred for 4 hours. The solvent was removed from the reaction solution under reduced pressure and distillation was performed under reduced pressure to obtain 65 g (yield of 64%) of a pale yellow liquid compound represented by the following Compound 5. Results of thermogravimetry analysis (TGA) and differential scanning calorimetry (DSC) on the compound represented by the following Compound 5 were as shown in FIG. 9 and FIG. 10, respectively.

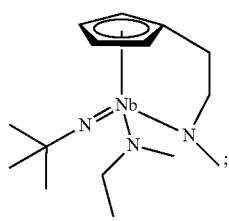

<Compound 5>

Boiling point (bp): 109° C. (0.4 torr);
Elemental analysis calcd for (C$_{15}$H$_{28}$N$_3$Nb): C, 52.48, H, 8.22, N, 12.24; found C, 52.39, H, 8.27, N, 12.21;
$^1$H-NMR (400 MHz, C$_6$D$_6$, 25° C.) δ 5.980, 5.812, 5.719, 5.708 (m, 4H, C$_5$H$_4$(CH$_2$)$_2$N(CH$_3$)), δ 4.149, 3.632, 2.515, 2.404 (m, 4H, C$_5$H$_4$(CH$_2$)$_2$N(CH$_3$)), δ 3.588 (m, 2H, N(CH$_2$CH$_3$)(CH$_3$)), δ 3.405 (s, 3H C$_5$H$_4$(CH$_2$)$_2$N(CH$_3$)), δ 3.223 (s, 3H, N(CH$_2$CH$_3$)(CH$_3$)), δ 1.268 (s, 9H, NC(CH$_3$)$_3$), δ 1.157 (t, 3H, N(CH$_2$CH$_3$)(CH$_3$)).

<Example 6> Preparation of (Cp(CH$_2$)$_2$N(CH$_3$))($^t$BuN)Nb(NMe$_2$)

Figure 11:
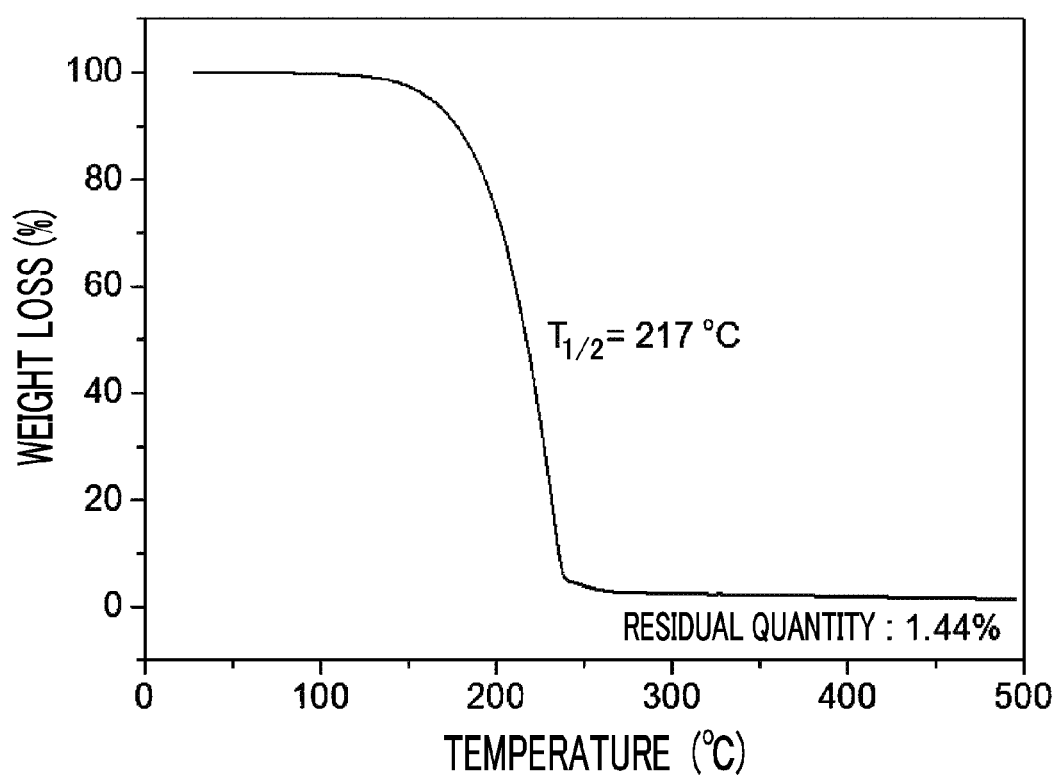
FIG. 11 is a graph showing a result of thermogravimetry analysis (TGA) on $(Cp(CH_2)_2N(CH_3))(^tBuN)Nb(NMe_2)$ in accordance with an example of the present disclosure.
Figure 12:
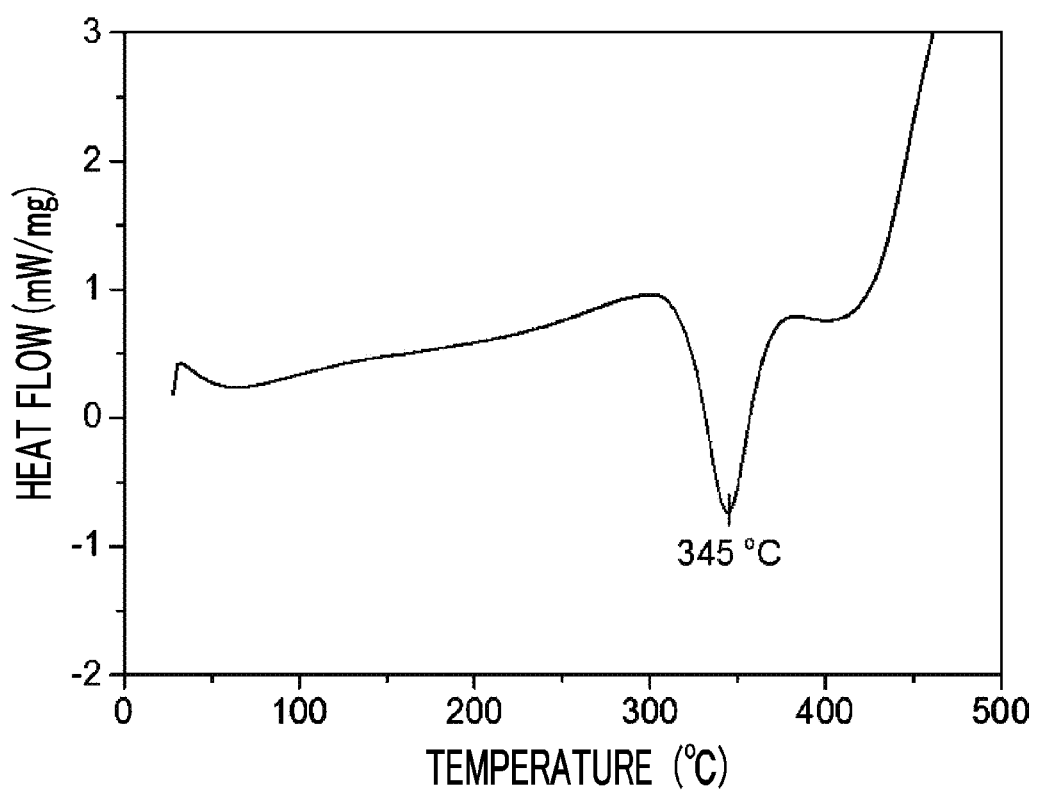
FIG. 12 is a graph showing a result of differential scanning calorimetry (DSC) on $(Cp(CH_2)_2N(CH_3))(^tBuN)Nb(NMe_2)$ in accordance with an example of the present disclosure.

100 g (0.337 mol, 1 equivalent) of tris(diethylamido)(tert-butylimido)tantalum [($^t$BuN)Nb(NMe$_2$)$_3$] and 300 mL of toluene were put into a flame-dried 500 mL Schlenk flask and then stirred at room temperature. After 41.6 g (0.337 mol, 1 equivalent) cyclopentadienylethylmethylamine [Cp(CH$_2$)$_2$NH(CH$_3$)] was dropwisely added to the flask at room temperature, the temperature of the reaction solution was raised to 60° C. and then the reaction solution was stirred for 4 hours. The solvent was removed from the reaction solution under reduced pressure and distillation was performed under reduced pressure to obtain 70 g (yield of 63%) of a pale yellow liquid compound represented by the following Compound 6. Results of thermogravimetry analysis (TGA) and differential scanning calorimetry (DSC) on the compound represented by the following Compound 6 were as shown in FIG. 11 and FIG. 12, respectively.

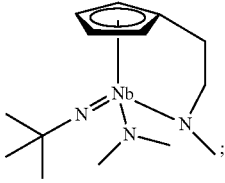

<Compound 6>

Boiling point (bp): 108° C. (0.4 torr);
Elemental analysis calcd for (C$_{14}$H$_{26}$N$_3$Nb): C, 51.07, H, 7.96, N, 12.76; found C, 52.01, H, 7.92, N, 12.81;
$^1$H-NMR (400 MHz, C$_6$D$_6$, 25° C.) δ 5.976, 5.811, 5.746, 5.679 (m, 4H, C$_5$H$_4$(CH$_2$)$_2$N(CH$_3$)), δ 4.188, 3.607, 2.530, 2.413 (m, 4H, C$_5$H$_4$(CH$_2$)$_2$N(CH$_3$)), δ 3.416 (s, 3H C$_5$H$_4$(CH$_2$)$_2$N(CH$_3$)), δ 3.325 (s, 6H, N(CH$_3$)$_2$), δ 1.275 (s, 9H, NC(CH$_3$)$_3$).

Figure 13:
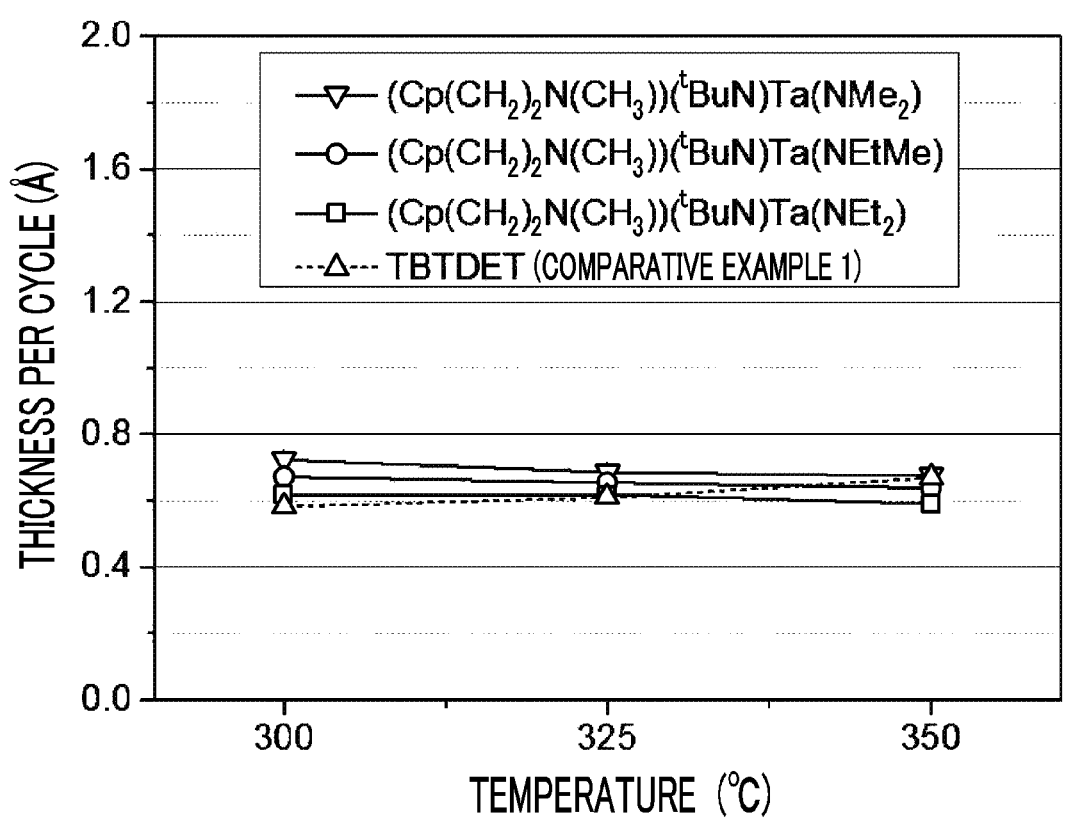
FIG. 13 shows film growth depending on the substrate temperature in atomic layer deposition using different Group 5 metal compound precursors in accordance with Example 7 and Comparative Example 1, respectively, of the present disclosure.

<Example 7> Formation of Tantalum Oxide Layer by Atomic Layer Deposition Using (Cp(CH$_2$)$_2$N(CH$_3$))($^t$BuN)Ta(N Et$_2$), (Cp(CH$_2$)$_2$N(CH$_3$))($^t$BuN)Ta(NEtMe), and (Cp(CH$_2$)$_2$N(CH$_3$))($^t$BuN)Ta(NMe$_2$) Compound and Ozone (O$_3$) Gas A test for forming a tantalum oxide layer by atomic layer deposition (ALD) using the compounds prepared in Example 1 to Example 3 as a precursor and ozone (O$_3$) gas was conducted. In this case, a silicon (Si) wafer was used as a substrate. The substrate was heated at a temperature of from 300° C. to 350° C. Further, each precursor compound in a stainless-steel container was heated at a temperature of 100° C., and argon (Ar) gas was allowed to pass through the container at a flow rate of 60 sccm to supply each precursor compound into an ALD reactor for performing atomic layer deposition. An internal pressure in the ALD reactor was maintained at 3 torr. An atomic layer deposition cycle in which after a gas of the precursor compound was supplied to the ALD reactor for 5 seconds, argon gas was supplied for 5 seconds and then, ozone (O₃) gas was supplied for 5 seconds and argon gas was supplied again for 5 seconds was repeated 200 times. The thickness per cycle of each tantalum oxide thin film formed according to the above-described process was as shown in FIG. 13. As shown in FIG. 13, it was observed that film growth per ALD source material supply cycle was generally uniform in the range of substrate temperature of from 300° C. to 350° C.

<Comparative Example 1> Formation of Tantalum Oxide Layer by Atomic Layer Deposition Using (tert-butylimido)tris(diethylamido)tantalum (TBTDET) [(ᵗBuN)Ta(NEt₂)₃] Compound and Ozone (O₃) Gas A tantalum oxide layer was formed by atomic layer deposition under the same conditions as in Example 7 except TBTDET was used as a precursor and the precursor compound in a stainless-steel container was heated at a temperature of 70° C. The film growth by atomic layer deposition depending on the substrate temperature was as shown in FIG. 13. Unlike the result of Example 7, more film growth was observed at a higher substrate temperature in the atomic layer deposition using TBTDET. This is because a thicker film is formed due to pyrolysis of TBTDET at 325° C. or 350° C., and when the pyrolysis occurs, a uniform-thickness tantalum oxide layer cannot be formed on a pattern having a very high aspect ratio at 325° C. or 350° C.

It is confirmed from Example 7 and Comparative Example 1 that atomic layer deposition using the compound gases prepared in Example 1 to Example 3, respectively, and ozone gas is more advantageous for the purpose of forming a uniform-thickness tantalum oxide layer on the entire surface of a substrate including severe unevenness, i.e., a high-aspect ratio pattern, at a substrate temperature of from 300° C. to 350° C. than atomic layer deposition using a TBTDET gas and ozone gas.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A Group 5 metal compound, represented by the following Chemical Formula 1:

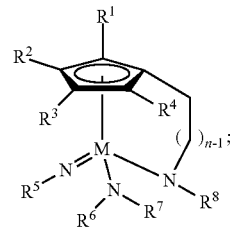

[Chemical Formula 1]

wherein in the Chemical Formula 1,
M is Ta or Nb,
each of $R^1$, $R^2$, $R^3$, and $R^4$ is independently hydrogen, or a linear or branched $C_{1-4}$ alkyl group,
$R^5$ is a linear or branched $C_{3-6}$ alkyl group,
each of $R^6$, $R^7$ and $R^8$ is independently a linear or branched $C_{1-4}$ alkyl group,
n is an integer of from 1 to 4, and
one carbon atom of the cyclopentadienyl group ring and the nitrogen atom of —NR⁸ are bridge-bonded to each other through the alkylene group.

2. The compound of claim 1,
wherein each of $R^1$, $R^2$, $R^3$, and $R^4$ is independently hydrogen, methyl group, or ethyl group.

3. The compound of claim 1,
wherein $R^5$ is n-propyl group, isopropyl group, n-butyl group, tert-butyl group, isobutyl group, sec-butyl group, n-pentyl group, tert-pentyl group, isopentyl group, sec-pentyl group, neopentyl group, or 3-pentyl group.

4. The compound of claim 1,
wherein each of $R^6$, $R^7$, and $R^8$ is independently methyl group or ethyl group.

5. A precursor composition for depositing a Group 5 metal-containing layer, comprising the Group 5 metal compound according to claim 1.

6. A method for depositing a Group 5 metal-containing layer, comprising forming a Group 5 metal-containing layer on a substrate using a precursor composition for depositing the Group 5 metal-containing layer of claim 5.

7. The method of claim 6,
wherein the Group 5 metal-containing layer is deposited by chemical vapor deposition or atomic layer deposition.

8. The method of claim 6,
wherein the substrate includes unevenness formed on the surface thereof.

9. A method for preparing a Group 5 metal compound represented by the following Chemical Formula 1, which comprises:
reacting a compound (R⁵N═)M(NR⁶R⁷)₃ represented by the following Chemical Formula 2 with a compound $R^1R^2R^3R^4Cp(CH_2)_nNHR^8$ represented by the following Chemical Formula 3:

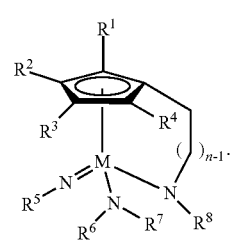

[Chemical Formula 1]

-continued

[Chemical Formula 2]

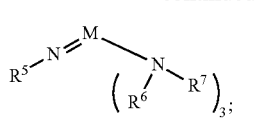

[Chemical Formula 3]

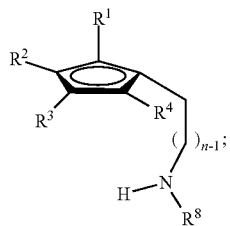

wherein in each of the above Formulas 1 to 3,
M is Ta or Nb,
each of $R^1$, $R^2$, $R^3$, and $R^4$ is independently hydrogen, or a linear or branched $C_{1-4}$ alkyl group,
$R^5$ is a linear or branched $C_{3-6}$ alkyl group,
each of $R^6$, $R^7$ and $R^8$ is independently a linear or branched $C_{1-4}$ alkyl group,
n is an integer of from 1 to 4, and
the Cp is a cyclopentadienyl group.

10. The method of claim 9,
wherein each of $R^1$, $R^2$, $R^3$, and $R^4$ is independently hydrogen, methyl group, or ethyl group.

11. The method of claim 9,
wherein $R^5$ is n-propyl group, isopropyl group, n-butyl group, tert-butyl group, iso-butyl group, sec-butyl group, n-pentyl group, tert-pentyl group, iso-pentyl group, sec-pentyl group, neopentyl group, or 3-pentyl group.

12. The method of claim 9,
wherein each of $R^6$, $R^7$, and $R^8$ is independently methyl group or ethyl group.

* * * * *